(12) United States Patent
Porta et al.

(10) Patent No.: US 7,338,777 B2
(45) Date of Patent: Mar. 4, 2008

(54) METHOD FOR DETERMINING THE BIOLOGICAL ACTIVITY OF DEFIBROTIDE

(75) Inventors: Roberto Porta, Cernobbio (IT); Franco Cattaneo, Goria Minore (IT); Laura Ferro, Milan (IT)

(73) Assignee: Gentium SPA, Villa Guardia (IT)

( * ) Notice: Subject to any disclaimer, the term of this patent is extended or adjusted under 35 U.S.C. 154(b) by 604 days.

(21) Appl. No.: 10/868,798

(22) Filed: Jun. 17, 2004

(65) Prior Publication Data
US 2005/0009131 A1    Jan. 13, 2005

Related U.S. Application Data

(63) Continuation-in-part of application No. PCT/EP02/13371, filed on Nov. 27, 2002.

(30) Foreign Application Priority Data
Dec. 17, 2001    (EP)    ................... 01830770

(51) Int. Cl.
*C12Q 1/37*    (2006.01)
(52) U.S. Cl. .......................................... 435/24; 514/44

(58) Field of Classification Search .................. 435/24; 514/44
See application file for complete search history.

(56) References Cited

U.S. PATENT DOCUMENTS 4,234,682 A    11/1980    Bartl et al.
5,231,006 A    7/1993    Kolde

FOREIGN PATENT DOCUMENTS

WO    WO 99/12935    *    3/1999
WO    WO 03/052130 A2    6/2003

OTHER PUBLICATIONS

Porta, R. et al; "High-Performance Liquid Chromatography Determination of Polydeoxyribonucleotides in Plasma: Its application to the Determination of Defibrotide's Pharmacokinetics in the Rabbit"; *Analytical Biochemistry*, vol. 204, pp. 143-146 (1992).

* cited by examiner

*Primary Examiner*—Ralph Gitomer
(74) *Attorney, Agent, or Firm*—Nixon & Vanderhye

(57) ABSTRACT

Method for determining the biological activity of defibrotide by a) bringing into contact defibrotide, plasmin and a substrate specific for the plasmin which, by reaction with the plasmin, provides a measurable product; and b) measuring the amount of product formed at successive times, to thereby determine the biological activity of the defibrotide.

17 Claims, 6 Drawing Sheets

Kinetics of release of pNA from the substrate S-2251, by means of plasmin which is activated and non-activated with defibrotide (concentration 0-100 µg/ml, 0-20 min.).

*Absorbance x 1000 (405 nm)* time (min)

Kinetics of release of pNA from the chromogenic substrate S-2251, by means of plasmin in the presence of defibrotide (concentration 0.5 µg/ml, 5 replicates)

*Absorbance x1000 (405 nm)*

*time (min.)*

TABLE 1

|   | Sample | a | b | $r^2$ |
|---|---|---|---|---|
| ● | 1 | 64,92 | 4,95 | 0,9898 |
| ○ | 2 | 63,42 | 4,68 | 0,9947 |
| ▼ | 3 | 68,10 | 4,56 | 0,9974 |
| ▽ | 4 | 65,25 | 4,82 | 0,9967 |
| ■ | 5 | 65,42 | 5,05 | 0,9894 |

Kinetics of release of pNA from the substrate S-2251, by means of plasmin in the presence of defibrotide (concentration 2.0 µg/ml, 5 replicates)

*Absorbance x1000 (405 nm)*

*time (min.)*

TABLE 2

|   | Sample | a | b | $r^2$ |
|---|---|---|---|---|
| ● | 1 | 37,39 | 7,28 | 0,9973 |
| ○ | 2 | 44,07 | 6,32 | 0,9987 |
| ▼ | 3 | 42,03 | 6,84 | 0,9977 |
| ▽ | 4 | 38,28 | 6,57 | 0,9997 |
| ■ | 5 | 40,86 | 6,71 | 0,9973 |

Kinetics of release of pNA from the substrate S-2251, by means of plasmin in the presence of defibrotide (concentration 8.0 µg /ml, 5 replicates)

*Absorbance x1000 (405 nm)*

*time (min.)*

TABLE 3

| | Sample | a | b | $r^2$ |
|---|---|---|---|---|
| ● | 1 | 38,21 | 8,76 | 0,9987 |
| ○ | 2 | 30,21 | 7,61 | 0,9995 |
| ▼ | 3 | 33,57 | 7,31 | 0,9983 |
| ▽ | 4 | 28,21 | 7,67 | 0,9994 |
| ■ | 5 | 21,89 | 8,32 | 0,9991 |

TABLE 4

| Defibritide conc. (μg/ml) | Replication | "b" | p-Nitroaniline μM/min |
|---|---|---|---|
| 0.5 | | 4.95 | 0.60 |
| 2.0 | 1 | 7.28 | 0.88 |
| 8.0 | | 8.76 | 1.06 |
| 0.5 | | 4.68 | 0.57 |
| 2.0 | 2 | 6.32 | 0.76 |
| 8.0 | | 7.61 | 0.92 |
| 0.5 | | 4.56 | 0.55 |
| 2.0 | 3 | 6.84 | 0.83 |
| 8.0 | | 7.31 | 0.88 |
| 0.5 | | 4.82 | 0.58 |
| 2.0 | 4 | 6.57 | 0.79 |
| 8.0 | | 7.67 | 0.93 |
| 0.5 | | 5.05 | 0.61 |
| 2.0 | 5 | 6.71 | 0.81 |
| 8.0 | | 8.32 | 1.01 |

METHOD FOR DETERMINING THE BIOLOGICAL ACTIVITY OF DEFIBROTIDE

This application is a Continuation-in-Part of Application No. PCT/EP02/13371 filed Nov. 27, 2002, the entire content of which is hereby incorporated by reference in this application, which claims priority to Application EPO 01830770.2 filed Dec. 17, 2001.

The present invention relates to a method for determining the biological activity of defibrotide and, more especially, relates to an indirect enzymatic method for determining the biological activity of defibrotide.

TECHNICAL FIELD OF THE INVENTION

Defibrotide (Merck Index, 1996, no. 2915) is a substance of natural origin which is obtained by extraction from animal organs and which is constituted by the sodium salt of polydeoxyribonucleotides having a low molecular weight. Defibrotide has been the subject of numerous pharmacological investigations which have suggested that it be applied in therapy as an anti-thrombotic agent (U.S. Pat. No. 3,829,567).

In addition, defibrotide has also been used successfully in the treatment of peripheral arteriopathies, in acute renal insufficiency (U.S. Pat. No. 4,694,134) or in acute myocardial ischaemia (U.S. Pat. No. 4,693,995).

Like other biological substances which are obtained by extraction, defibrotide also is subject to a limited variability of composition which is typical of natural biopolymers. A classical example of this situation is provided by heparin whose variability from batch to batch in terms of chain length, molecular weight, composition, degree of sulphatation, etc. is well known. The consequence of this is that the same amounts by weight of defibrotide could in fact be non-equivalent from the point of view of a specific biological activity.

The process of extraction, isolation and purification cannot per se ensure absolute reproducibility of the product, precisely owing to its intrinsic biopolymeric nature.

However, if well controlled, it is possible to reduce this variability: for that purpose, studies have been made of standardized industrial processes for isolating defibrotide by extraction from organs, such as, for example, that described in United States patent U.S. Pat. No. 4,985,552.

The product obtained according to the above-mentioned process is characterized by the determination of some specific physico-chemical parameters, such as, for example, electrophoretic mobility, the coefficient of extinction, optical rotatory power and reversible hyperchromicity. However, those parameters depend basically on the structure of defibrotide and are not capable of providing information on the biological activity thereof.

As far as we know, the only methods that have been reported to be used hitherto to evaluate the biological activity of defibrotide are the fibrin plate test and the thromboelastographic recording of the euglobulin lysis time [Prino G., Mantovani M., Niada R., Coccheri S., Butti A., Indagini preliminari sull'attività fibrinolitica, nell'animale e nell'uomo, di una nuova sostanza presente in diversi organi animali, Simposio Internazionale: La ricerca scientifica nell'industria farmaceutica in Italia, Rome, 2-4 Oct. 1975— Il Farmaco, Ed. Prat.) (1969), 24,552-561].

However, the above-mentioned methods are characterized by considerable experimental complexity, by unsatisfactory reproducibility and precision and, in the specific case of thromboelastographic recording, by a response linearity limited to very restricted concentration ranges.

Hitherto, therefore, no truly valid, precise and reproducible methods have been known for determining the biological activity of defibrotide.

We have developed a simple and reliable method for determining the biological activity of defibrotide, which enables the samples obtained by extraction to be controlled and therefore enables medicinal preparations based on defibrotide to be standardized.

The method to which the present invention relates enables the specific biological activity of defibrotide to be determined in comparison with a reference standard with a high degree of precision, speed and reproducibility.

BRIEF DESCRIPTION OF THE DRAWINGS

The invention will now be further illustrated with reference to the accompanying drawings, in which.

DETAILED DESCRIPTION OF PREFERRED EMBODIMENTS

Figure 1:
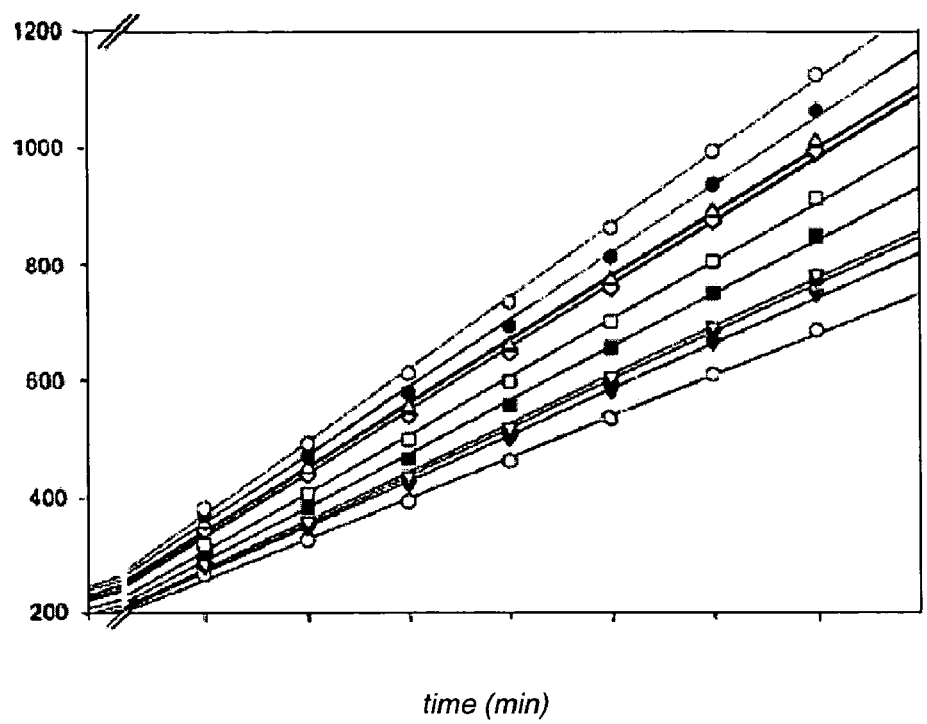
FIG. 1 is a plot showing the kinetics of release of pNA from the substrate S-2251, by means of plasmin which is activated and non-activated with defibrotide (concentration 0-100 µg/ml, 0-20 min.)

The present invention therefore relates to a method for determining the specific biological activity of samples of defibrotide, which method comprises the steps of:

a) bringing into contact defibrotide, plasmin and a substrate specific for the plasmin which, by reaction with the plasmin, provides a measurable product and b) measuring the amount of product formed at successive times.

The method of the invention is an indirect in vitro method for determining the activity of defibrotide, which is based on the functional interactions between defibrotide and plasmin.

It is known from the literature that plasmin is a proteolytic enzyme in the cascade of coagulation/fibrinolysis capable of cleaving fibrin, fibrinogen and other plasma proteins.

The enzymatic activity of plasmin is normally determined by various standard in vitro tests. One of the most commonly used methods is the determination by spectrophotometry or fluorimetry of the chromogenic or fluorogenic compounds that are freed by the action of plasmin on suitable substrates [Haemostasis, (1978), 7, 138-145]. Peptide substrates having the formula $A_1$-$A_2$-$A_3$-X are generally used in which $A_1$ and $A_2$ are amino acids that are predominantly non-polar, $A_3$ is lysine or arginine and X represents the measurable freed compound, for example para-nitroaniline (pNa) or 2-naphthylamine (NA) [Haemostasis, (1978), 7, 146-149]. In addition to the above-mentioned peptide substrates, success has been achieved using other, simpler, compounds, such as, for example, p-nitrobenzyl-p-toluenesulphonyl-L-arginine [Haemostasis, (1978), 7, 105-108].

In those tests, the rate at which the compound X is released into the incubation medium is proportional to the activity (International Units) of plasmin present in the sample.

It has now been discovered, and this is the principle on which the present invention is based, that in the plasmin-evaluation tests described above, defibrotide increases the rate of release of compound X proportionally to its concentration.

The method to which the present invention relates provides first of all for bringing the sample of defibrotide, the plasmin and the substrate for the plasmin into contact with one another.

The defibrotide sample used for the determination according to the invention is generally prepared by extraction from organs in accordance with known procedures, such as described, for example, in U.S. Pat. No. 4,985,552 which has already been mentioned.

A batch of normal industrially manufactured defibrotide was chosen as the reference sample (standard) and was used to prepare the calibration curves in accordance with the method of the present invention.

In general, the present method provides precise and accurate measurements of defibrotide even in the presence of contaminants, such as, for example, RNA, heparin, degraded defibrotide (defibrotide from which purin or pyrimidine has been removed) or ethanol, provided they are in concentrations, generally less than 10% by weight, such as not to impair the system.

In addition to permitting the determination of defibrotide, the method also allows the determination of other biologically equivalent substances derived from defibrotide, such as, for example, deaminated defibrotide or, more simply, defibrotide denatured by heating.

The present method is sufficiently sensitive to detect concentrations of defibrotide lower than or equal to 0.1 µg/ml (final concentration in the determination system) and, generally, expresses good correlation up to maximum concentration values higher than or equal to 100 µg/ml.

The plasmin used is generally any mammalian plasmin, such as, for example, bovine, porcine or human plasmin, with a preference for human plasmin.

However, although plasmin is the enzyme of choice, the use of other equivalent enzyme systems, such as, for example, precursors of plasmin, such as plasminogen, or plasmin-analogue enzymes which are chemically related and have a similar functionality, falls within the scope of the present invention.

In the method of the present invention, the substrate for the plasmin may be understood as being any substrate specific for plasmin which, under the conditions of the method, frees a detectable hydrolysis product X.

Depending on the nature of the detectable group X, alternative systems of detection commonly known to the person skilled in the art can be adopted equally well. Spectrophotometric or fluorimetric detection systems are particularly advantageous, especially spectrophotometric systems.

The substrates generally used are ones that are specific for plasmin. It is preferable to use peptides of the formula $A_1$-$A_2$-$A_3$-X, in which $A_1$ and $A_2$ are amino acids that are predominantly non-polar, $A_3$ is lysine or arginine and X is the detectable group. Examples of those substrates are Val-Leu-Lys-pNa, Val-Phe-Lys-pNa or pyroGlu-Phe-Lys-pNa in which the group X detectable by spectrophotometry is para-nitroaniline (pNA). Other suitable substrates, for example Val-Gly-Arg-2NA, contain 2-naphthylamine, which is measurable by fluorimetry. A particularly preferred substrate is the compound H-D-Valyl-L-Leucyl-L-Lysine-p-nitroaniline (H-D-Val-Leu-Lys-pNA).

The plasmins and the specific substrates used for determining defibrotide are generally commercially available.

The determination method of the present invention is carried out by placing the reagents and the defibrotide sample in aqueous solution, at a specific pH and molarity.

In particular, the concentration of the plasmin may vary, usually from 0.0016 to 0.20 I.U./ml, preferably from 0.0064 to 0.050 I.U./ml, and even more preferably is approximately 0.0125 I.U./ml.

However, as regards the substrate for the plasmin, concentrations of from 0.3 to 4 mM, preferably from 2.5 to 3.5 mM and advantageously of 3 mM, are generally used in the case of a chromogenic substrate, while concentrations of from 0.05 to 0.15 mM are used in the case of a fluorogenic substrate.

The determination method of the invention, like other enzymatic methods, is sensitive to the pH of the medium.

In fact, it cannot generally be applied at extreme pH values where the enzymatic system would be inactivated.

It is also preferable for the pH of the medium not to undergo variation at any time during the period when measurements are being taken, and therefore the solution is generally buffered with buffer systems selected from those normally used in plasmin-determination tests. Suitable buffer systems may be, for example, phosphate buffer, citrate buffer or tris(hydroxymethyl)aminomethane hydrochloride (TRIS) buffer. The operation is preferably carried out in the presence of TRIS.

In the present method it is usually preferred to maintain the pH of the medium in a range of approximately from 7 to 8, more preferably at approximately 7.4.

In addition, it is preferred to maintain the concentration of the buffer system in a range of from 10 to 200 mM, preferably at approximately 50 mM.

The method of the invention for determining defibrotide provides that the plasmin, the substrate for the plasmin, and the defibrotide be mixed. In particular, in order to enable the measurements provided for by the method to be carried out correctly, it is preferable to add the plasmin or the specific substrate, or both, to the buffered solution containing the defibrotide sample before the start of the measuring stage. The substrate for the plasmin is preferably added last.

An important parameter in the present method of determination is the temperature. It is preferable for the same temperature to be maintained throughout the entire duration of the measurements and for all of the samples determined, both as regards the construction of the reference curves and during the measuring stage. To that end, it is preferable to use temperature controlled apparatus and also, where necessary, it is possible to proceed with several sets of measurements, changing the position of the samples appropriately in order to ensure that the system has maximum thermal homogeneity.

Generally, this method of determination is applied in a temperature range of, for example, from 25 to 40° C., preferably from 35 to 39° C., and even more preferably at 37° C.

According to the present invention, measurement of the concentration of compound X released in the medium by the action of the plasmin starts when all of the reagents have been added and continues for a predetermined time and at a predetermined frequency as a function of the chemical nature of X and of the detection system.

Similarly to other methods of biological determination, the method of the invention also provides for a calibration stage and a measuring stage which are preferably carried out in parallel in order to reduce as far as possible the incidence of experimental variability.

The calibration stage comprises the acquisition of the absorbance data relating to the samples at known increasing concentrations of defibrotide (standard), the statistical reprocessing of those data and the extrapolation of calibration curves, which express the correlation between the increase in the rate of the enzymatic reaction of the invention and the concentration of defibrotide present in the medium. In the measuring stage, owing to the correlation obtained in the calibration stage, it is possible to determine the unknown biological activities of samples of defibrotide on the basis of the absorbance values measured and processed under the same conditions.

In more detail, the experimental protocol generally provides for the preparation of several samples, both standard and unknown, at various known concentrations of defibrotide. The defibrotide samples are prepared by progressive dilution of the mother solutions in accordance with a predetermined dilution factor.

In the present method, it is preferred to prepare at least 5 concentrations of the standard and 5 concentrations of the sample to be tested, preparing 5 replicates, or more preferably 10 replicates, for each concentration of the standard and, similarly, for each concentration of the test sample, generally for successive 1:2 dilutions of mother solutions.

Both the standard and test-sample concentrations of defibrotide are generally from 0.1 to 100 μg/ml, preferably from 0.3 to 50 μg/ml, more advantageously from 0.5 to 8 μg/ml.

The concentrations of the test sample are preferably of the same order of magnitude as the concentrations of the standard.

In accordance with the above illustration, the measurements for each concentration are preferably carried out on two microplates where the position of each sample, the standard and the test sample, respectively, at corresponding concentration is preferably reversed from one plate to the other. According to this scheme for the arrangement of the samples, which is explained in more detail in the experimental part, for each concentration of both standard and test-sample defibrotide, at least 5 or, preferably, 10 absorbance values are measured for each time.

The set of measurements described above are taken at predetermined times, that is to say, first of all at time $t_0$, that is to say, when all of the components have been added, before the enzymatic reaction of the invention has started, and subsequently at precise intervals and for a period of time sufficient to acquire the necessary data.

Preferably, the absorbance measurements are continued up to a maximum of 90 minutes, with readings taken every 1-10 minutes. More advantageously, the readings are taken at time to and subsequently, from 20 to 50 minutes, every 5 minutes. The photometric absorbance readings are performed at a wavelength which depends on the nature of the detectable group X freed in the course of the enzymatic hydrolytic reaction. In the specific case in which X is p-NA, the absorbance is measured at 405 nm.

The absorbance readings of the standard and unknown defibrotide samples, known as raw data, generally originate directly from the same apparatus that provides for the reading operation; they are tabulated in such a manner that an absorbance value is expressed for each time and well.

The raw data are then processed, using, for example, the Spread Sheet—Microsoft Excel®. This first processing operation leads to the calculation of the average absorbance and of the associated standard deviation, at each time and for each set of readings, each set comprising at least 5 and preferably 10 replicates for each concentration of both standard and test-sample defibrotide.

Further statistical processing of the data is carried out with a program of the Sigma Plot Computer Program® type (SPSS, Chicago, USA) which takes the mathematical relationship existing between the absorbance values of the samples and the time, for each set of defibrotide concentrations, to obtain straight lines whose slope is proportional to the concentration of defibrotide.

To be more precise, in the interval in which there is response linearity, preferably from 20 to 50 minutes, and for each of the 5 or, preferably, 10 replicates of the same concentration, the program calculates a regression line which is characterized by a coefficient of linear regression "b", by a coefficient of determination "$r^2$" and by the intercept "a".

The straight lines produced in accordance with the present procedure generally have a good correlation expressed by high values of $r^2$, generally not less of 0.97, preferably $r^2 \geq 0.99$.

The data produced by the program can be reproduced as tabulated digital data or can be represented graphically, for each set of concentrations.

As illustrated in FIG. 1, by placing the time on the abscissa and the absorbance on the ordinate, straight lines will be obtained whose slope "b" will be proportional to the rate of enzymatic reaction: by increasing the concentration of defibrotide, the rate of hydrolysis and, proportionally, the value of "b" will increase. Finally, the slope values, calculated as described above for each set of replicates of standard defibrotide and test-sample defibrotide, are correlated with the decimal logarithm of the concentration of defibrotide to which they relate.

Graphically, that correlation gives rise to a sigmoid for the standard and a sigmoid for the test sample (FIG. 2); the central portions of the sigmoid have two straight lines which are generally parallel and the distance between which is a function of the difference in biological activity between the test sample and the standard.

In this interval of linearity, the power of the unknown defibrotide sample compared with that of the standard is determined in accordance with the parallel-line biological determination methodology described by Finney D J, Statistical Method in Biological Assay, 2nd ed. Ch. Griffin, London.

That methodology can be applied when, as in the present invention, the biological response is a linear function of the logarithm of the concentration of the substance to be determined and when there is parallelism and linearity between the straight lines associated with the standard and, respectively, unknown concentrations.

Preferably, the statistical processing of the data, the calculation of the power ratio and, thus, the determination of the unknown activity of defibrotide are carried out using dedicated softwares constructed on the basis of the abovementioned methodology.

However, statistical data-processing, which, in chemical analysis in general and in the present method more particularly, enables the incidence of errors and experimental variability to be minimized, is not binding for the method of the invention and simply represents a method of evaluating results which is well known to the person skilled in the art and which is commonly used in the field.

The present invention relates also to kits for determining the biological activity of defibrotide in accordance with the method of the invention, comprising at least:

a) a measured amount of a substrate for the plasmin as defined above and b) a measured amount of plasmin.

Preferred kits comprise from 20 to 30 mg of substrate specific for plasmin per unit of plasmin, and even more preferably 25 mg of substrate per unit of plasmin.

According to the present invention, kits comprising H-D-Val-Leu-Lys-pNA, as the substrate specific for plasmin, and human plasmin, are particularly advantageous.

The kits according to the present invention may also contain a buffered aqueous solution, preferably a solution buffered with TRIS.HCl 50 mM, at pH 7.4.

Optionally, the kits of the invention also comprise a measured amount of defibrotide (standard) in order to permit control measurements.

In a preferred embodiment of the present invention, the standard solutions and the solutions of the samples of defibrotide to be determined are introduced into the respective wells of the microplates. The plasmin solution is prepared at the moment of use and is distributed in the wells containing defibrotide and, finally, the solution containing the substrate for the plasmin is added. The microplate is then placed in the thermostated reader and, after rapid agitation, readings of the system's absorbance are taken at predetermined intervals and for the predetermined period of time. The raw data obtained are then processed, thus determining the unknown activities of the defibrotide samples.

Those and other aspects of the invention will be better illustrated in the following Examples which are not, however, to be regarded as limiting the invention.

EXAMPLES

The following materials were used in the Examples given here:

Apparatus

Detector for a microplate having 96 wells MRX TCII (Dynex Technologies, Chantilly, Va., USA), thermostated and equipped with an enzymatic kinetics program.

Microplates having 96 wells with a flat base (Greiner L., Kremunster, Austria, cat. 655101)

Pipettes with continuous volume adjustment Pipetman P200 (30-200 µl) and 8×200 (20-200 µl) and 200-µl tips of certified quality (Gilson, Milan, Italy)

pH-meter PHM85 Radiometer (Analitica De Mori, Milan, Italy)

Programs

Microsoft Excel® (Microsoft Corporation, Redmond, Wash., USA)

Sigma Plot Computer Program® (SPSS, Chicago, USA)

Substances

Defibrotide (Gentium)

Human plasmin, 1 unit, P-4895 (Sigma Aldrich, Milan, Italy)

Chromogenic substrate S-2251, 820332-39 (Chromogenix Instrumentation Laboratory S.p.A., Milan, Italy)

Tris(hydroxymethyl)aminomethane (TRIS), 255285-9 (Sigma-Aldrich, Milan, Italy)

1N HCl 1090571000 (Merck)

1N NaOH 1091411000 (Merck)

Solutions

TRIS-HCl buffer 2.42 g of TRIS are dissolved in distilled water and diluted to a volume of 100 ml. 16 ml of 1N HCl are added to the solution followed by more distilled water to give a final volume of 400 ml. The pH of this last solution is 7.40. If the values are different, the pH is corrected to give the desired value by the addition of 1N HCl or 1N NaOH.

Plasmin Solution

One unit (1 I.U.) of human plasmin is dissolved in 4 ml of TRIS-HCl buffer at 0° C. Operating always in ice, the solution is then subdivided into aliquots of 200 µl which are preserved at −20° C. in 10-ml plastics test tubes.

Solution of Chromogenic Substrate S-2251

25 mg of S-2251 are dissolved in 15.15 ml of distilled water and preserved at +4/+8° C.

Standard Defibrotide Solutions

Preparation of the Standard Solutions (Final) concentrations of from 0.1 to 100 µg/ml 60 mg of defibrotide are dissolved in 3 ml of TRIS-HCl buffer and diluted 1:15 with the TRIS-HCl buffer solution. The solution so obtained, having a concentration of 1.333 mg/ml, is subjected to successive 1:2 dilutions to give defibrotide solutions having a concentration of 666 µg/ml, 333 µg/ml and 166 µg/ml. This last solution, which is used as the mother solution, is further diluted to obtain solutions having concentrations of 83.33 µg/ml, 41.67 µg/ml, 33.33 µg/ml, 25 µg/ml, 16.66 µg/ml, 8.33 µg/ml, 5 µg/ml, 2.5 µg/ml, 1.66 µg/ml, 0.83 µg/ml, 0.5 µg/ml and finally 0.16 µg/ml.

(Final) concentrations of from 0.5 to 8 µg/ml 60 mg of defibrotide are dissolved in 3 ml of TRIS-HCl buffer and diluted 1:1500 with the TRIS-HCl buffer solution. The solution so obtained, having a concentration of 13.33 µg/ml, is subjected to successive 1:2 dilutions to give defibrotide solutions having a concentration of 6.66 µg/ml, 3.33 µg/ml, 1.66 µg/ml and 0.83 µg/ml, respectively.

Procedure

150 µl of each of the standard defibrotide solutions described above are taken and introduced into the wells of the microplates.

The plasmin solution is then prepared rapidly by adding, at 0° C., 3.8 ml of TRIS-HCl buffer to the test tube containing 0.2 ml of human plasmin solution. The whole is agitated gently until dissolution has occurred, and 50 µl are taken and introduced into the wells of the microplate, followed by 50 µl of S-2251 for each well.

The microplate, placed in the MRX TCII reader set at 37° C., is agitated for approximately 10 seconds; the absorbance readings are carried out at 405 nm, at the initial time $t_0$ and subsequently every two minutes in the interval from 10 to 20 minutes, in accordance with the enzymatic kinetics program.

The experimental data measured for defibrotide concentrations from 0.1 to 100 μg/ml are then processed (Excel and Sigma Plot programs) and represented in a graph (regression lines) as shown by way of example in the following FIGS. 1 and 2.

Figure 2:
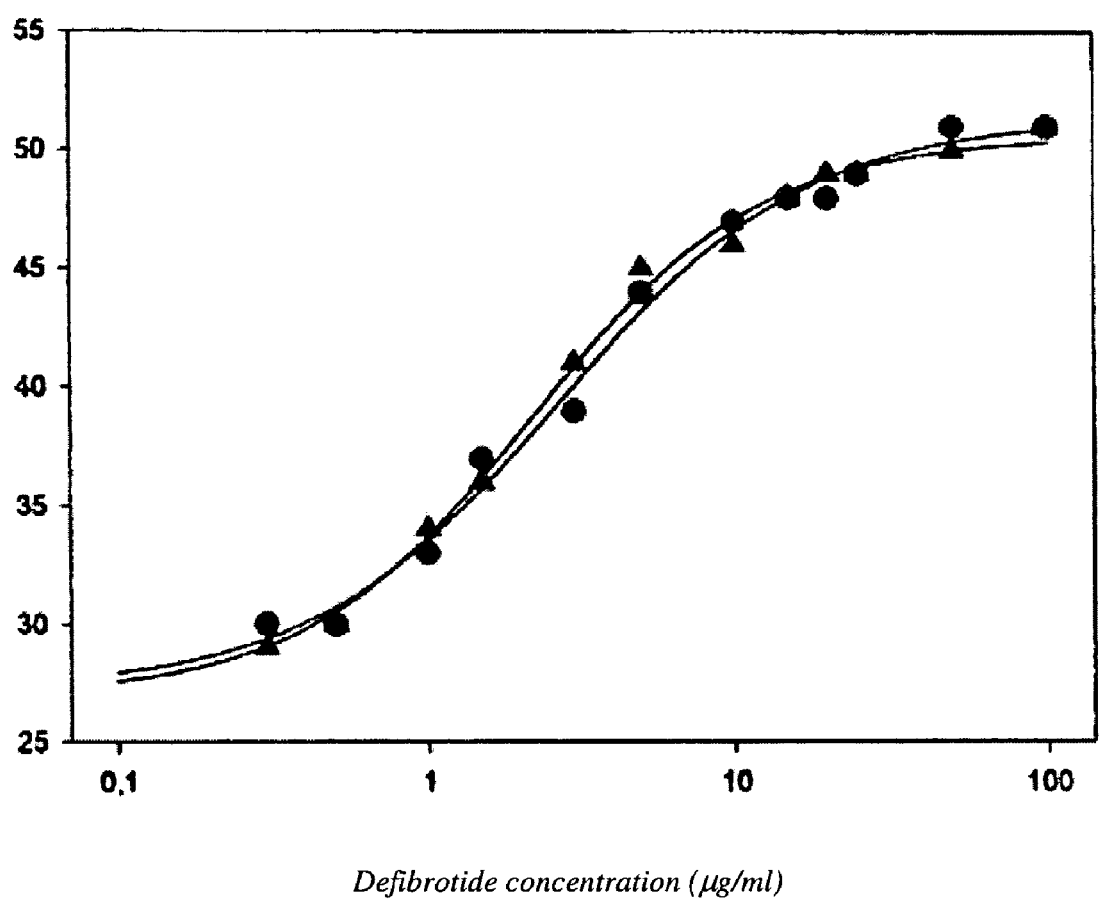
FIG. 2 is a plot illustrating the sigmoid that arises in relation to a standard and test sample of defibrotide.

The values of the angular coefficients b (slope) of the straight lines corresponding to the standard and the test sample of defibrotide (FIG. 1) are plotted with respect to the defibrotide concentrations (logarithmic scale) (FIG. 2).

As can be seen from the graph, a linear response which enables a straight line to be identified is obtained in the central portion of the curve. In that interval of linearity, the power of the unknown defibrotide sample is determined in comparison with the standard, in accordance with the parallel-line biological determination methodology mentioned already and described by Finney D J, Statistical Method in Biological Assay, 2nd ed. Ch. Griffin, London. In order for this methodology to be applicable, it is important for there to be, in addition to linearity, parallelism between the straight lines relating to the standard and, respectively, to the defibrotide to be tested.

The test for determining the biological activity of an unknown defibrotide sample, compared with standard defibrotide, is carried out preferably by using concentrations that give rise to the rectilinear portion of the sigmoid determined above. In particular, concentrations of standard and unknown defibrotide in the range from 0.5 to 8 μg/ml are preferred.

The arrangement, in the wells of the plate, of the replicates of the various defibrotide concentrations for the standard and for the sample under examination is given hereinafter.

|   | Standard defibrotide | | | | | | Test sample | | | | | |
|---|---|---|---|---|---|---|---|---|---|---|---|---|
|   | 1 | 2 | 3 | 4 | 5 | 6 | 7 | 8 | 9 | 10 | 11 | 12 |
| A | — | — | — | — | — | — | — | — | — | — | — | — |
| B | — | 0.5 | 8.0 | 4.0 | 2.0 | 1.0 | 1.0 | 2.0 | 4.0 | 8.0 | 0.5 | — |
| C | — | 1.0 | 0.5 | 8.0 | 4.0 | 2.0 | 2.0 | 4.0 | 8.0 | 0.5 | 1.0 | — |
| D | — | 2.0 | 1.0 | 0.5 | 8.0 | 4.0 | 4.0 | 8.0 | 0.5 | 1.0 | 2.0 | — |
| E | — | 4.0 | 2.0 | 1.0 | 0.5 | 8.0 | 8.0 | 0.5 | 1.0 | 2.0 | 4.0 | — |
| F | — | 8.0 | 4.0 | 2.0 | 1.0 | 0.5 | 0.5 | 1.0 | 2.0 | 4.0 | 8.0 | — |
| G | — | — | — | — | — | — | — | — | — | — | — | — |
| H | — | — | — | — | — | — | — | — | — | — | — | — |

The standard defibrotide solutions are placed in columns 2-6 while the samples of defibrotide to be determined are placed in columns 7-11, at the concentrations indicated. In the second plate, the positions of the samples are preferably reversed. The outer columns and lines of the microplate are not used for the determination process but are filled with water in order to ensure maximum temperature homogeneity in all of the system.

The microplate, placed in the MRX TCII reader set at 37° C., is agitated for approximately 10 seconds; the absorbance readings are taken at 405 nm, at the initial time $t_0$ and subsequently every 5 minutes for a period from the 20th to the 50th minute, in accordance with the enzymatic kinetics program.

The absorbance values measured are then processed (Excel and Sigma Plot programs), tabulated and represented in a graph (regression lines).

It was then possible to calculate the power ratio and to determine the activity of the unknown sample of defibrotide compared with the standard, using the same system of calculation as that described above.

By way of example the Tables (1, 2 and 3) and the graphs (FIGS. 3, 4 and 5) relating to defibrotide samples, tested at a concentration of 0.5 μg/ml, 2.0 μg/ml and 8.0 μg/ml, respectively, are given hereinafter.

In addition, considering the data reported in Table 1, 2 and 3, we have also calculated the μM/min of p-Nitroaniline released by plasmin acting on the chromogenic substrate in the presence of Defibrotide.

Figure 3:
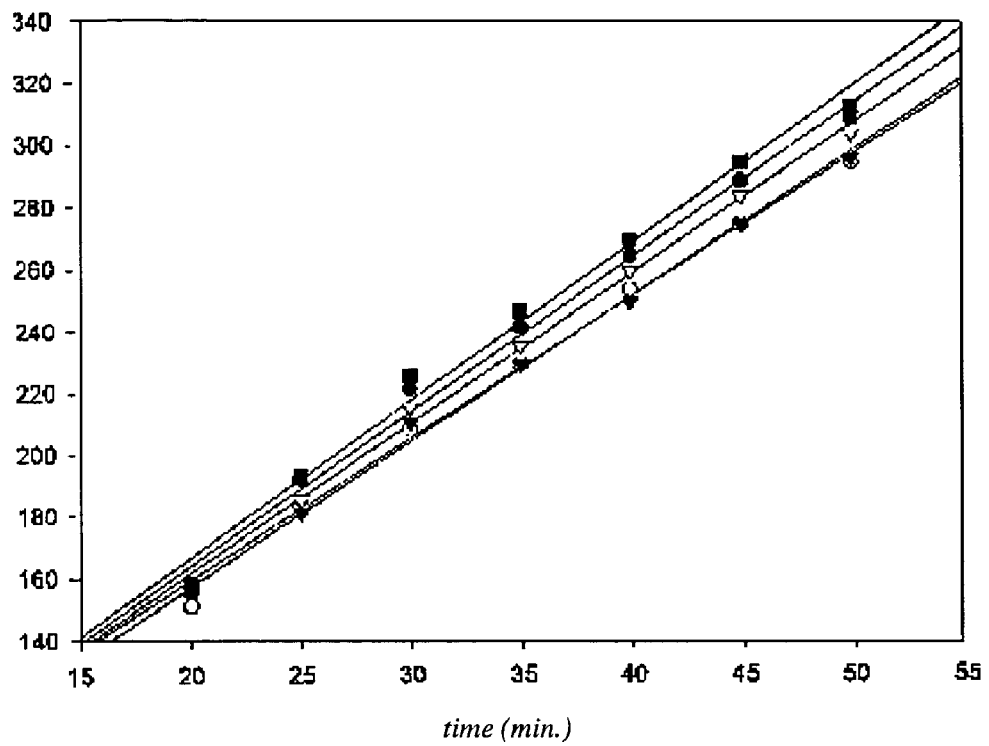
FIG. 3 is a plot showing the kinetics of release of pNA from the chromogenic substrate S-2251, by means of plasmin in the presence of defibrotide (concentration 0.5 µg/ml, 5 replicates)
Figure 4:
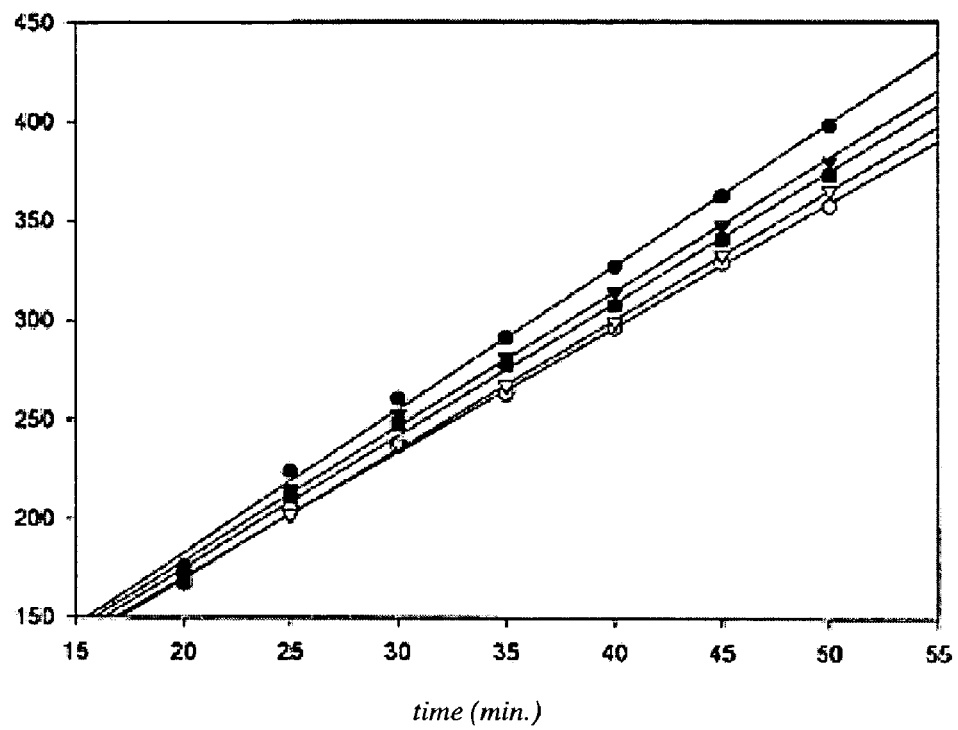
FIG. 4 is a clot showing the kinetics of release of DNA from the substrate S2251, by means of plasmin in the presence of defibrotide (concentration 2.0 µg/ml, 5 replicates)
Figure 5:
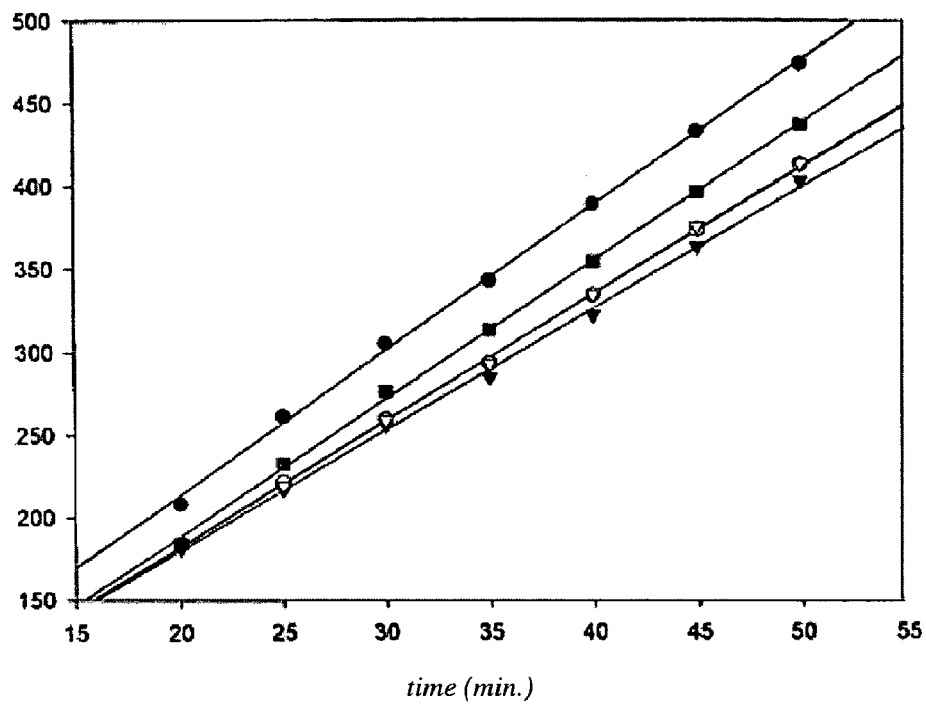
FIG. 5 is a plot showing the kinetics of release of pNA from the substrate S-2251, by means of plasmin in the presence of defibrotide (concentration 8.0 µg/ml, 5 replicates)

The "b" values reported in Tables 1, 2 and 3, namely the slopes of the kinetics curves, represent the ΔAbs/min×1000 (usually, just to avoid numbers with commas, the scale for the spectrophotometric readings in FIGS. 3, 4 and 5 was multiplied by 1000; as a consequence, the real spectrophotometric absorbance reading is obtained dividing "b" by 1,000).

Knowing from the literature, the Molar Extinction Coefficient for p-Nitroaniline (8,270 $M^{-1}cm^{-1}$, corresponding to 0.008270 Unit of Absorbance per μM of p-Nitroaniline) it follows that:

1μM p-Nitroaniline: 0.008270 (Absorbance)=X μM p-Nitroaniline: Spectrophotometric Reading ("b"/1000)

In this way we have calculated the micromoles of p-Nitroaniline released in the previous experiments, whose value are reported in table 4.

Figure 6:
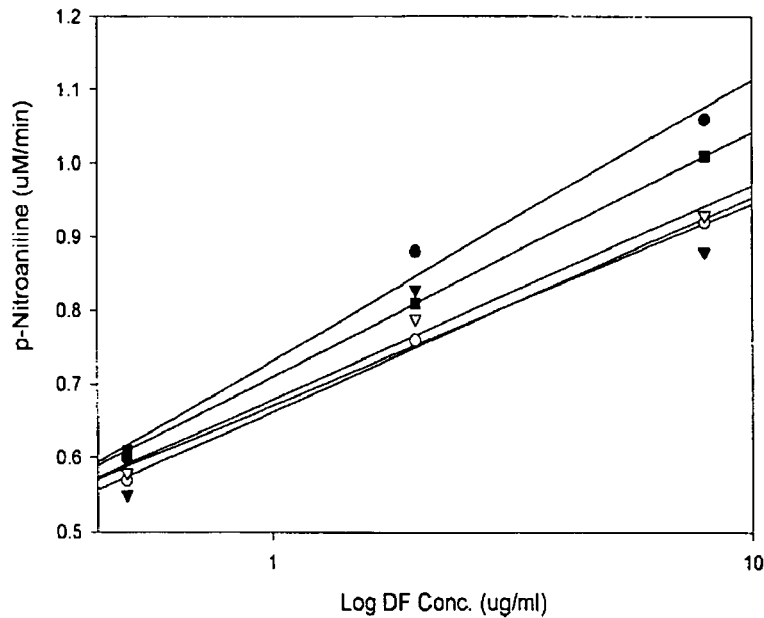
FIG. 6 is a plot showing the correlation between defibrotide concentrations and the µM of p-nitroaniline released in the corresponding semi-logarithmic graph.

The correlations between Defibrotide concentrations and the μM of p-Nitroaniline released are showed in the corresponding semi-logarithmic graph (FIG. 6).

The regression lines determined by the linear correlation for the 5 replications are represented by the equations:

| μM/min p-Nitroaniline=0.7317+0.3820 log X | Replication 1 |
|---|---|
| μM/min p-Nitroaniline=0.6625+0.2907 log X | Replication 2 |
| μM/min p-Nitroaniline=0.6708+0.2741 log X | Replication 3 |
| μM/min p-Nitroaniline=0.6792+0.2907 log X | Replication 4 |
| μM/min p-Nitroaniline=0.7100+0.3323 log X | Replication 5 |

More in general, the equation describing the p-Nitroaniline release is:

$$pNA(\mu M/min)=a+b\log X$$

where:
a=0.6908±0.0291 (Mean±Standard Deviation)
b=0.3140±0.0437 (Mean±Standard Deviation)
X=concentration of defibrotide (μg/ml)

or
"a" (intercept) could range from 0.6625 to 0.7317
"b" (slope) could range from 0.2741 to 0.3820.

The invention claimed is:

1. A method for determining the biological activity of defibrotide, which comprises the steps of:
   a) bringing into contact defibrotide, plasmin and a substrate specific for the plasmin which, by reaction with the plasmin, provides a measurable product; and
   b) measuring the amount of product formed at successive times, to thereby determine the biological activity of the defibrotide.

2. The method according to claim 1, wherein the plasmin is a mammalian plasmin.

3. The method according to claim 2, wherein the plasmin is human plasmin.

4. The method according to claim 1, wherein the substrate specific for the plasmin is a compound of formula $A_1\text{-}A_2\text{-}A_3\text{-}X$ in which $A_1$ and $A_2$ are non-polar amino acids, $A_3$ is lysine or arginine and X is the measurable product.

5. The method according to claim 4, wherein the measurable product X is selected from the group consisting of para-nitroaniline and 2-naphthylamine.

6. The method according to claim 4, wherein the substrate for the plasmin is H-D-Valyl-L-Leucyl-L-Lysine-p-nitroaniline.

7. The method according to claim 4, wherein the measurable product X is measured by spectrophotometry.

8. The method according to claim 1, wherein the plasmin has a concentration of from 0.0064 to 0.050 I.U./ml and the substrate for the plasmin has a concentration of from 2.5 to 3.5 mM.

9. The method according to claim 8, wherein the concentration of plasmin is 0.0125 I.U./ml and the concentration of the substrate for the plasmin is 3 mM.

10. The method according to claim 1, wherein the reaction is carried out in a reaction medium which is an aqueous solution buffered to a pH of from 7 to 8.

11. The method according to claim 10, wherein the reaction medium is an aqueous solution buffered to a pH of 7.4.

12. The method according to claim 1, wherein the temperature is maintained at from 35 to 39° C.

13. The method according to claim 12, wherein the temperature is maintained at 37° C.

14. The method according to claim 1, wherein the concentration of the substrate for the plasmin is from 0.3 to 4 mM.

15. The method according to claim 14, wherein the concentration of the substrate for the plasmin is from 2.5 to 3.5 mM.

16. The method according to claim 14, wherein the concentration of the substrate for the plasmin is 3 mM.

17. A method for determining the biological activity of defibrotide according to claim 1, which method comprises the steps of:
  a) determining the rate of release of the measurable product during the course of the enzymatic reaction of both a standard sample and a test sample;
  b) correlating, mathematically and/or graphically, the rate of release with the corresponding defibrotide concentration to obtain the biological activity of the test sample of defibrotide.

* * * * *